United States Patent [19]

Nadolink

[11] Patent Number: 5,693,889
[45] Date of Patent: Dec. 2, 1997

[54] METHOD FOR MONITORING SURFACE STRESS

[75] Inventor: Richard H. Nadolink, Portsmouth, R.I.

[73] Assignee: The United States of America as represented by the Secretary of the Navy, Washington, D.C.

[21] Appl. No.: 716,664

[22] Filed: Aug. 27, 1996

[51] Int. Cl.⁶ .................................................. G01L 1/24
[52] U.S. Cl. .......................... 73/800; 73/777; 73/841
[58] Field of Search ........................ 73/768, 775, 778, 73/801, 577, 598, 627, 777, 776, 800, 841

[56] References Cited

U.S. PATENT DOCUMENTS

| | | | |
|---|---|---|---|
| 3,620,589 | 11/1971 | Dudderar | 73/800 X |
| 4,109,515 | 8/1978 | Swenson, Jr. | 73/800 |
| 4,119,380 | 10/1978 | Raftopoulos et al. | 73/800 |
| 4,346,600 | 8/1982 | Johnson et al. | 73/768 |
| 4,553,436 | 11/1985 | Hansson | 73/514.33 |
| 4,722,600 | 2/1988 | Chiang | 73/800 X |
| 4,789,236 | 12/1988 | Hodor et al. | 73/800 X |
| 4,805,461 | 2/1989 | Gupta et al. | 73/800 |
| 4,912,355 | 3/1990 | Noel et al. | 73/800 X |
| 4,962,669 | 10/1990 | Gernhart et al. | 73/800 |
| 5,128,537 | 7/1992 | Halg | 73/705 X |
| 5,199,298 | 4/1993 | Ng et al. | 73/54.01 |
| 5,511,428 | 4/1996 | Goldberg et al. | 73/777 |

*Primary Examiner*—Elizabeth L. Dougherty
*Attorney, Agent, or Firm*—Michael J. McGowan; Michael F. Oglo; Prithvi C. Lall

[57] ABSTRACT

A piece of single crystal silicon is embedded in a material such that the silicon is flush with the surface thereof. The silicon is illuminated with infrared radiation having a wavelength in the range of 800–1100 nanometers. Isochromatic fringe patterns projected from the silicon are monitored as a direct indication of the amount of stress experienced at the surface.

5 Claims, 1 Drawing Sheet

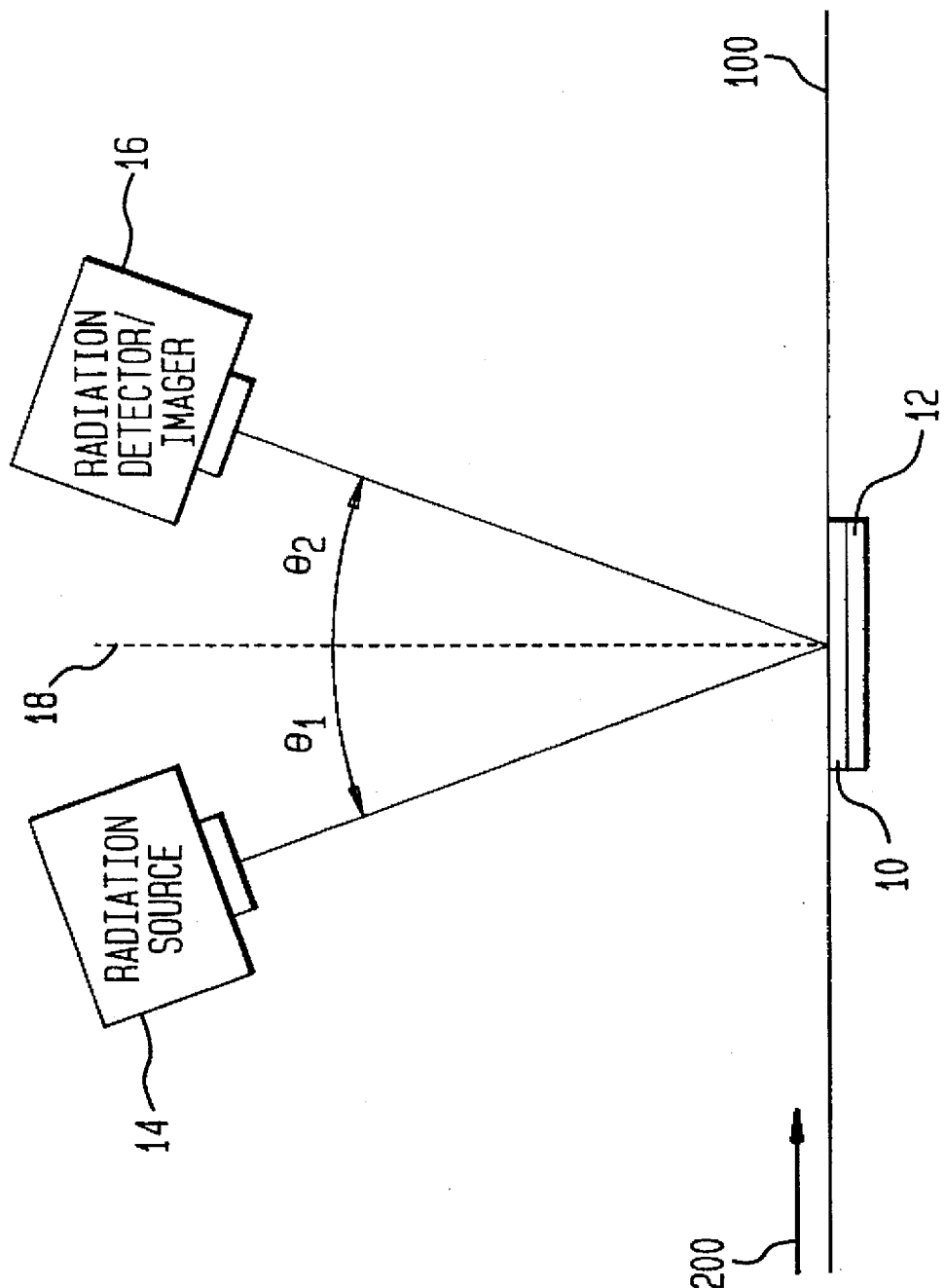

METHOD FOR MONITORING SURFACE STRESS

STATEMENT OF GOVERNMENT INTEREST

The invention described herein may be manufactured and used by or for the Government of the United States of America for Governmental purposes without the payment of any royalties thereon or therefor.

CROSS-REFERENCE TO RELATED PATENT APPLICATIONS

This patent application is co-pending with two related patent applications entitled "Photoelastic Stress Sensor", Ser. No. 08/605,291, filed Jan. 17, 1996, and "System for Monitoring Surface Stress and Other Conditions in Structures" (Navy Case No. 77286), filed the same date and by the same inventor as this patent application.

BACKGROUND OF THE INVENTION (1) Field of the Invention

The present invention relates generally to methods of monitoring stress in structures, and more particularly to a method for monitoring shear stress at a structure's surface.

(2) Description of the Prior Art

Shear stress experienced at a structure's surface due to a flow of fluid or gas can be determined indirectly by measuring the velocity profile next to the surface, and then taking the material derivative. Mathematically, this is expressed by the relationship $$\tau = \mu \frac{du}{dy} \bigg]_{y \to 0} \quad (1)$$

where $\tau$ is the shear stress at the surface;

$\mu$ is the viscosity of the gas or liquid;

u is the streamwise velocity; and y is the vertical distance from the surface.

While many methods exist to make direct measurements of $\mu$, u, and y, this is not a direct measurement of surface stress $\tau$.

Another indirect method of measuring stress is through hot wire anemometry where a thin wire or film is attached to the surface and heated externally through a control instrument (e.g., a wheatstone bridge). The flow over the surface cools the wire or film and the amount of supply voltage necessary to control a constant temperature is related to the surface shear stress by King's Law.

Methods of direct measurement of surface stress often require a floating element to be provided as part of the surface. A strain gauge is used to measure the movement of the floating element in the presence of flow. The floating element, no matter how small, must maintain a physical and electrical connection to and through the surface in question. Because of the difficulties associated with maintaining such physical and electrical connections, measurements can be contaminated by the connection geometry. Thus, the resulting stress measurement includes the drag on the element due to flow plus the non-zero "tear" drag or thrust that occurs due to the connection mechanisms.

Other direct measurement methods require the illumination of active elements located on a surface of the material being examined. However, the use of active element coatings, e.g., liquid crystal coatings, requires that the coating element be electrically energized before measurements can be taken. This requires connections that could contaminate the flow. Furthermore, liquid crystal coatings can be affected by the ambient temperature of the surrounding flow.

SUMMARY OF THE INVENTION

Accordingly, it is an object of the present invention to provide a method of monitoring stress at the surface of a material.

Another object of the present invention is to provide a method that provides for the direct measurement of surface stresses caused by a flow of a liquid or gas.

Still another object of the present invention is to provide a method that can be used to monitor flow-induced surface stress without interrupting the flow.

Other objects and advantages of the present invention will become more obvious hereinafter in the specification and drawings.

In accordance with the present invention, a method of monitoring stress at the surface of a material is provided. A piece of single crystal silicon is embedded in the material such that the silicon is flush with the surface. The silicon is illuminated with infrared radiation having a wavelength in the range of 800–1100 nanometers. Isochromatic fringe patterns projected from the silicon are monitored directly. The fringe patterns serve as a direct indication of the amount of stress experienced at the surface of the material.

BRIEF DESCRIPTION OF THE DRAWING(S)

Other objects, features and advantages of the present invention will become apparent upon reference to the following description of the preferred embodiments and to the drawings, wherein:

The sole FIGURE is a schematic view of an apparatus configured for monitoring shear stress at the surface of a material as caused by a flow of liquid or gas over the surface of the material in accordance with the method of the present invention.

DESCRIPTION OF THE PREFERRED EMBODIMENT(S)

Referring now to the sole FIGURE, the present invention will be described for the application of monitoring and measuring shear stress experienced at the surface of a material due to a flow over such surface. The surface to be examined is referenced by numeral 100 and the flow causing the stress to be detected and measured is referenced by flow arrow 200. As will become apparent from the following description, surface 100 is representative of any surface exposed to a flow such as an air, land or undersea vehicle, or a static structure such as a building, bridge, etc. Flow arrow 200 is representative of any liquid or gaseous flow that may induce stress at surface 100.

In accordance with the present invention, a small piece or wafer 10 of semiconductor grade, single crystal silicon is embedded in surface 100. Wafer 10 is in contact with the structure forming surface 100 and, typically, is made flush with surface 100 so that it is not directly affected by flow 200 and so that wafer 10 does not disturb flow 200. Wafer 10 is preferably, but not necessarily, backed by a mirror 12 or other reflective surface. A radiation source 14 and radiation detector/imager 16 are positioned remotely from surface 100. The radiation source 14 referred to is a conventional, commercially available product for use as a component in various electrooptical systems. More specifically, in accordance with the present invention, a source 14 is employed which is capable of illuminating wafer 10 with near-infrared radiation in the 800–1100 nanometer wavelength range. The radiation detector/imager 16 referred to is also a conventional, commercially available product capable of focusing in the context of the distance between detector/imager 16 and surface 100. A variety of such source and detector/imager devices are listed in the product catalogue of Edmund Scientific Company, Barrington, N.J.

Illumination by source 14 and monitoring by detector/imager 16 typically occurs in a plane that is normal to wafer 10. As shown, illumination from source 14 can occur along angle $\theta_1$, with respect to dashed line 18 representative of a line normal to wafer 10. Monitoring of wafer 10 would be accomplished by focusing detector/imager 16 from a position on the same or opposite side of line 18 along angle $\theta_2$ where $\theta_1$ and $\theta_2$ can be acute angles equivalent or different in magnitude. Alternatively, both the illumination of wafer 10 and monitoring (i.e., observation and/or imaging) of the resulting effects can occur directly above wafer 10 along line 18.

The principle of operation of the present invention depends upon the birefringent phenomenon. Many materials are optically sensitive to stress and strain, i.e. they possess the optical properties of polarizing light when under stress and of transmitting light or the principal stress planes with velocities dependent on the stresses. Transmission of stress planes is known as birefringence or double refraction. When wafer 10 is subjected to the specified radiation from source 14, the birefringent effect causes the light to emerge refracted into two orthonormal planes. Because the velocities of light propagation are different in each direction, the light waves experience a phase shift. When the light waves are recombined at detector/imager 16, regions of stress where the wave phases cancel appear black, and regions of stress where the wave phases combine appear light. Therefore, in photoelastic surfaces where complex, fast changing or 3-D stress distributions are present, light and dark fringe patterns (isochromatic fringes) are projected from wafer 10. The fringe patterns are direct manifestations of stress which can be observed and/or imaged by detector/imager 16. The use of mirror 12 aids in the direct monitoring of the fringe patterns from positions normal to wafer 10 or positions angularly displaced from normal line 18 as shown in the FIGURE. A quantitative measure of surface stress can thus be achieved by calibrating images of the fringe patterns with their respective known levels of stress.

In order to stimulate the above described photoelastic effect, it is necessary to make wafer 10 transparent. The crystal structure of semiconductor grade, single crystal silicon can be made optically transparent by radiation having a wavelength between 800–1100 nanometers.

The advantages of the present invention are numerous. The semiconductor grade, single crystal silicon requires no electrical stimulation. Thus, it is well suited to be embedded in a surface that is to be examined for flow-induced stress since the flow need not be disturbed. The present invention provides for direct measurement of stress with no moving parts. The single crystal silicon is a material that is highly corrosion resistant. In addition, the single crystal silicon can be activated and read from positions that are remote from the surface in question over a variety of angles of illumination and observation. The single crystal silicon is easily conformed in size and shape to the surface to be examined. The simplicity of the present invention results in an inexpensive approach to monitoring and measuring surface stress in a material that can be, but need not be, flow-induced.

The present invention could be adapted for use in the measurement and monitoring of stresses induced in essentially all types of structures. The completely passive nature of the embedded wafer allows for remote monitoring continuously or periodically. An example of this would be the application of the embedded wafer in a bridge structure at a critical stress point. The wafer could be monitored remotely through the optical process described above. The level of induced stress could be obtained by comparison with previous or ground truth measurements. The present invention is a simple and inexpensive approach that can be extended to monitor Changes in stress in the full range of wind or water tunnel type environments i.e., subsonic, supesonic, etc. For example, the necessary conditions of team focus may be transmitted through transparent test sections of wind or water tunnel facilities of all kinds, and also through viewing windows of towing tanks and basins, where hydrodynamic models (containing the embedded sensors) are being evaluated. The present invention could also monitor changes in stress on the actual surface of virtually any structure, e.g., submarines, aircraft, buildings, bridges, automobiles, spacecraft, rockets, undersea vehicles, etc. In addition, the present invention would allow a silicon-based sensor to be used in a dual mode. For example, the silicon substrate of a semiconductor pressure transducer could be used to monitor stress as described above while the pressure transducer functioned in its normal pressure sensing capacity. This would make it possible to use one sensor to obtain a variety of measurements simultaneously for a structure in question.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A method of monitoring stress at the surface of a material, comprising the steps of:

embedding a piece of single crystal silicon in the material such that said piece of single crystal silicon is flush with the surface;

placing a reflective surface between said piece of single crystal silicon and the material;

illuminating said piece of single crystal silicon with infrared radiation having a wavelength in the range of 800–1100 nanometers; and monitoring isochromatic fringe patterns projected from said piece of single crystal silicon as a result of said step of illuminating, wherein said isochromatic fringe patterns are a direct indication of an amount of stress at the surface of the material.

2. A method of monitoring stress at the surface of a material, comprising the steps of:

embedding a piece of single crystal silicon in the material such that said piece of single crystal silicon is flush with the surface;

illuminating said piece of single crystal silicon with infrared radiation having a wavelength in the range of 800–1100 nanometers, wherein said step of illuminating occurs from a first position that forms a first angle with respect to a line normal to said piece of single crystal silicon; and monitoring isochromatic fringe patterns projected from said piece of single crystal silicon as a result of said step of illuminating, wherein said isochromatic fringe patterns are a direct indication of an amount of stress at the surface of the material, and wherein said step of monitoring occurs from a second position that forms a second angle with respect to said line, said first angle and said second angle being equal in magnitude, and further wherein said first position and said second position lie along a plane normal to said piece of single crystal silicon.

3. A method of monitoring shear stress at the surface of a material due to a flow over the surface, comprising the steps of:

backing a single crystal silicon semiconductor wafer with a mirror;

embedding said wafer so backed in the material such that said wafer is flush with the surface of the material;

illuminating said wafer through said fluid flow with radiation having a wavelength in the range of 800–1100 nanometers; and monitoring isochromatic fringe patterns projected from said wafer as a result of said step of illuminating, wherein said isochromatic fringe patterns are a direct indication of an amount of stress at the surface of the material caused by said fluid flow.

4. A method according to claim 3 wherein said steps of illuminating and monitoring occur along a line normal to said wafer.

5. A method according to claim 3 wherein said steps of illuminating and monitoring occur on opposing sides of a line normal to said wafer.

* * * * *